(12) United States Patent
Jou et al.

(10) Patent No.: US 10,912,777 B2
(45) Date of Patent: Feb. 9, 2021

(54) DIPYRIDAMOLE FOR USE IN TREATING SLC29A2 NUCLEAR-EXPRESSING CANCER

(71) Applicant: Academia Sinica, Taipei (TW)

(72) Inventors: Yuh-Shan Jou, Taipei (TW); Roger Shen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/470,952

(22) PCT Filed: Dec. 19, 2017

(86) PCT No.: PCT/US2017/067294
§ 371 (c)(1),
(2) Date: Jun. 18, 2019

(87) PCT Pub. No.: WO2018/118910
PCT Pub. Date: Jun. 28, 2018

(65) Prior Publication Data
US 2019/0350933 A1    Nov. 21, 2019

Related U.S. Application Data

(60) Provisional application No. 62/437,666, filed on Dec. 22, 2016.

(51) Int. Cl.
*A61K 31/519*     (2006.01)
*A61P 35/04*      (2006.01)
*A61K 31/44*      (2006.01)

(52) U.S. Cl.
CPC ........... *A61K 31/519* (2013.01); *A61K 31/44* (2013.01); *A61P 35/04* (2018.01)

(58) Field of Classification Search
CPC ........ A61K 31/519; A61K 31/44; A61P 35/04
See application file for complete search history.

(56) References Cited

U.S. PATENT DOCUMENTS 5,215,744 A * 6/1993 Suzuki ............... A61K 38/21
424/85.4
2014/0235631 A1  8/2014 Bunt et al.

OTHER PUBLICATIONS

Zhang et al., JBUON, 2015;20(1):218-222 (Year: 2015).*
Chen et al., Hepatology, 2010; 52(5):1690-1701 (Year: 2010).*
International Search Report for PCT/US2017/067294, dated Mar. 20, 2018.
Written Opinion of International Search Authority for PCT/US2017/067294, dated Mar. 20, 2018.
Grane-Bolacieras et al "Novel nuclear hENT2 isoforms regulate cell cycle progression via controlling nucleoside transport and nuclear reservoir" Cell. Mel. Life Sci. (2016) 73"4559-4575.

* cited by examiner

*Primary Examiner* — San Ming R Hui
(74) *Attorney, Agent, or Firm* — Hsiu-Ming Saunders; Intellectual Property Connections Inc.

(57) ABSTRACT

A pharmaceutical composition comprising (i) a therapeutically effective amount of an inhibitor of the oncogene SLC29A2; and (ii) a pharmaceutically acceptable carrier, for use in suppressing proliferation, occurrence, and metastasis of cancer cells overexpressing the oncogene SLC29A2 in a cancer patient, and/or prolonging cancer patient survival. The inhibitor of the oncogene SLC29A2 may be at least one selected from the group consisting of dipyridamole, dilazep, draflzine, nitorbenzylthioinosine, and the derivatives thereof. The composition for use may further comprise sorafenib for the same use.

19 Claims, 11 Drawing Sheets

Specification includes a Sequence Listing.

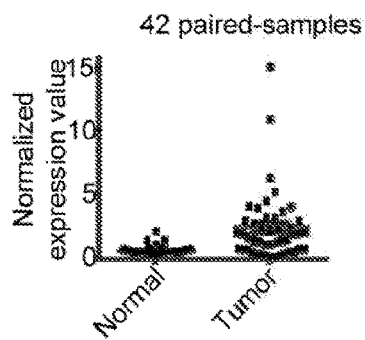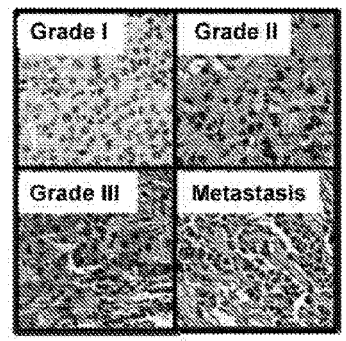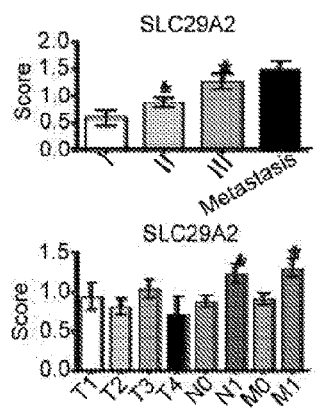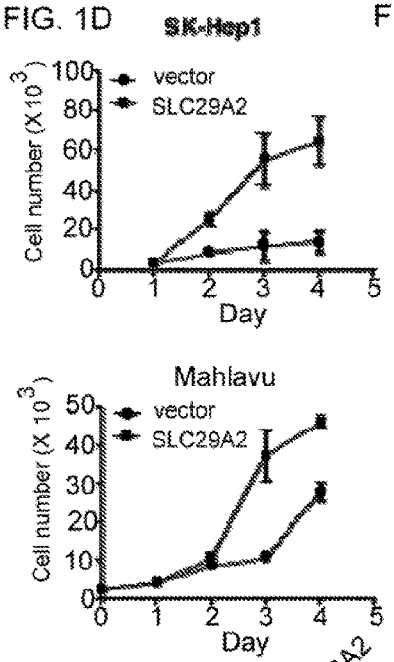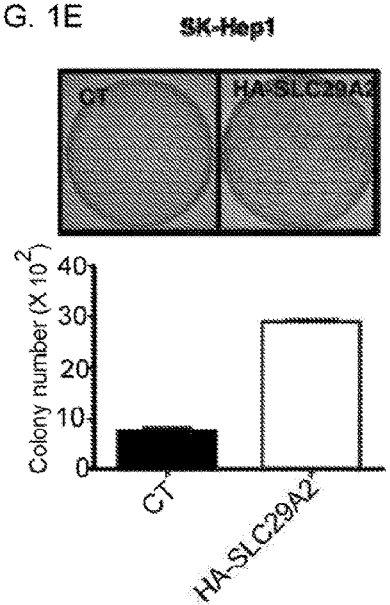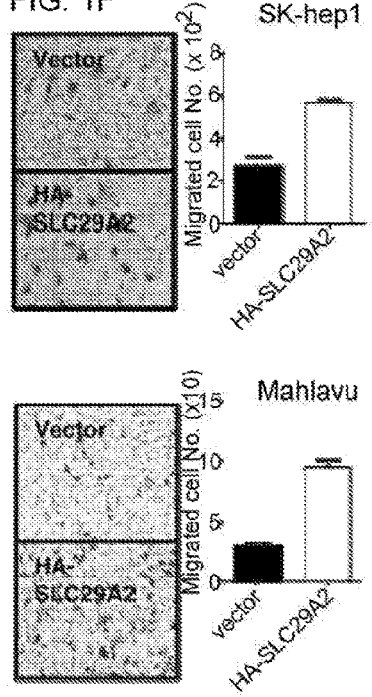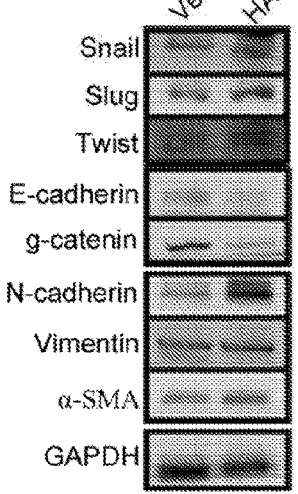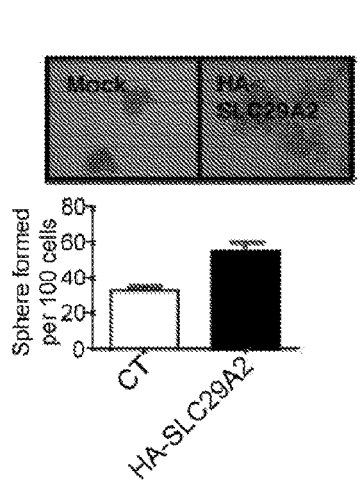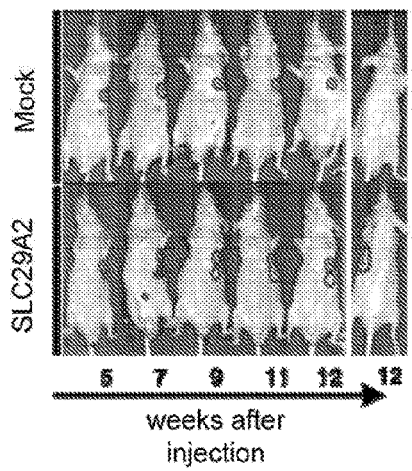

FIG. 2A
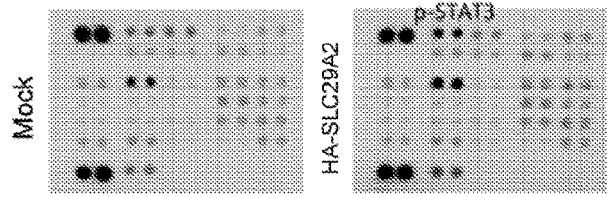
FIG. 2B
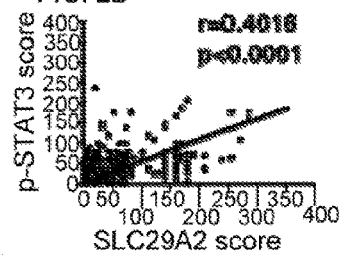
FIG. 2C
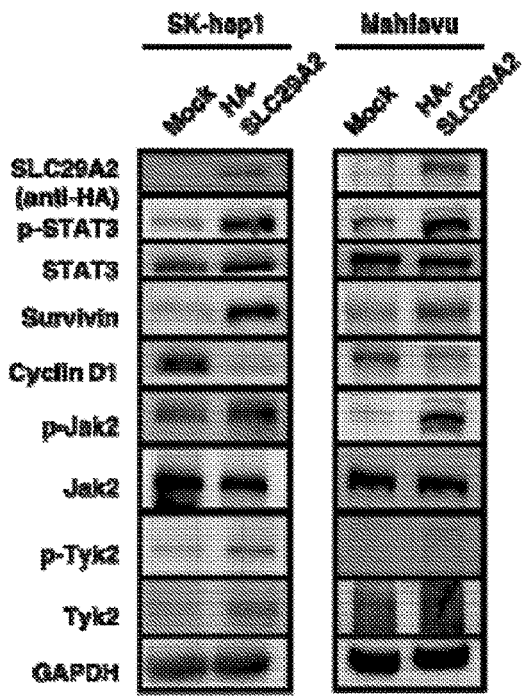
FIG. 2D
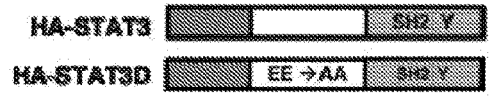
FIG. 2E
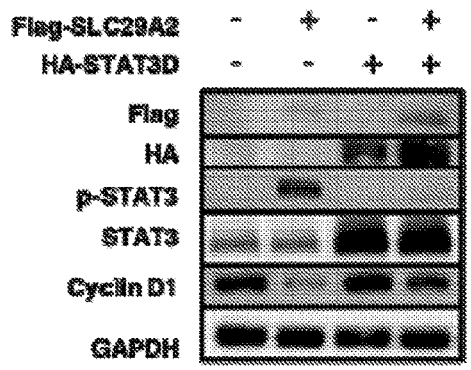
FIG. 2F
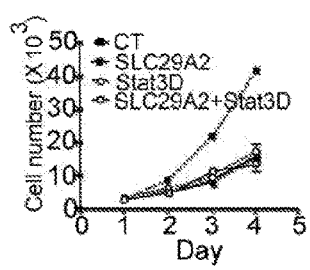
FIG. 2G  FIG. 2H  FIG. 2I
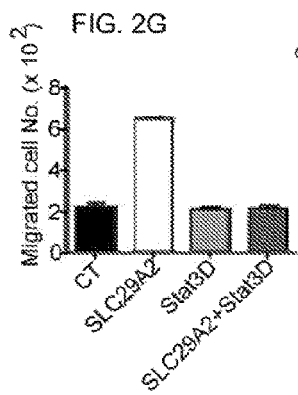
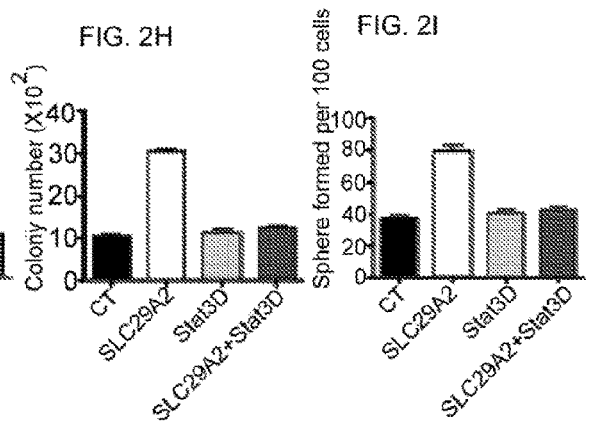

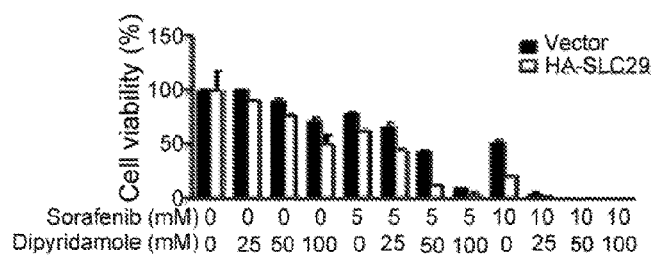
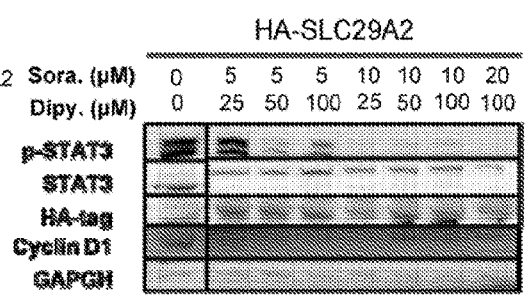
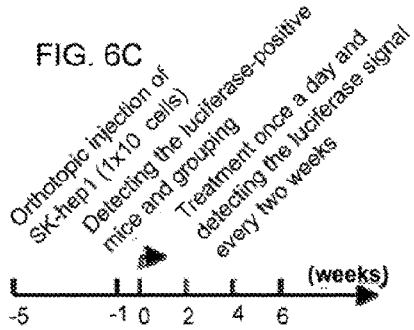
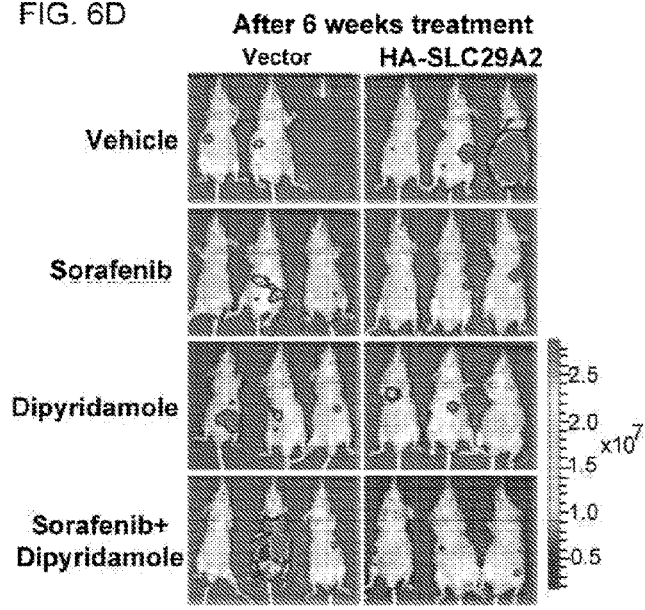
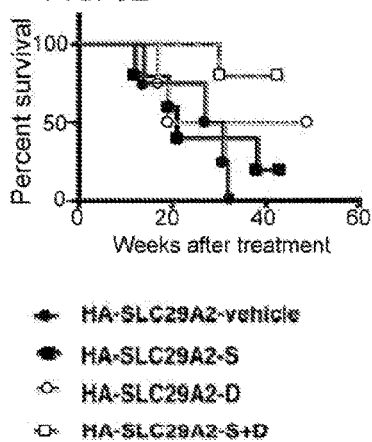

FIG. 8

Table 1

| Tissue type | Amplified/Total (%) | (%) |
|---|---|---|
| Salivary gland | 2/2 | 100.0 |
| Upper aerodigestive tract | 16/31 | 51.6 |
| Biliary tract | 3/7 | 42.9 |
| Oesophagus | 9/26 | 34.6 |
| Liver | 9/27 | 33.3 |
| Urinary tract | 7/24 | 29.2 |
| Breast | 12/56 | 21.4 |
| Bone | 5/24 | 20.8 |
| Pancreas | 8/44 | 18.2 |
| stomach | 6/38 | 15.8 |
| prostate | 1/7 | 14.3 |
| lung | 24/169 | 14.2 |
| soft tissue | 2/17 | 11.8 |
| ovary | 5/47 | 10.6 |
| thtroid | 1/11 | 9.1 |
| haematopoietic and lymphoid tissue | 13/175 | 7.4 |
| large intestine | 3/56 | 5.4 |
| endometrium | 1/28 | 3.6 |
| skin | 2/59 | 3.4 |
| central nervous system | 1/50 | 2.0 |
| autonomic ganglia | 0/17 | 0.0 |
| kidney | 0/21 | 0.0 |
| pleura | 0/9 | 0.0 |
| small intestine | 0/1 | 0.0 |
| Total | 130/946 | 13.7 |

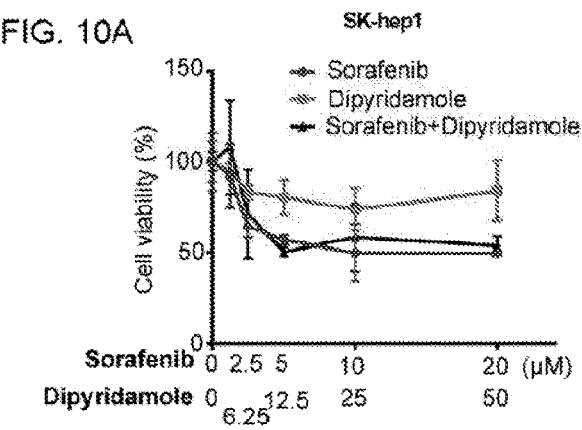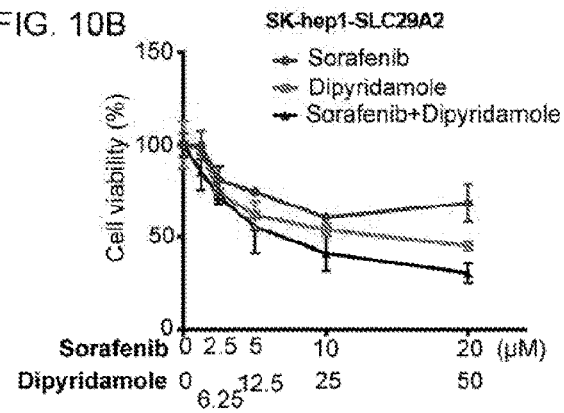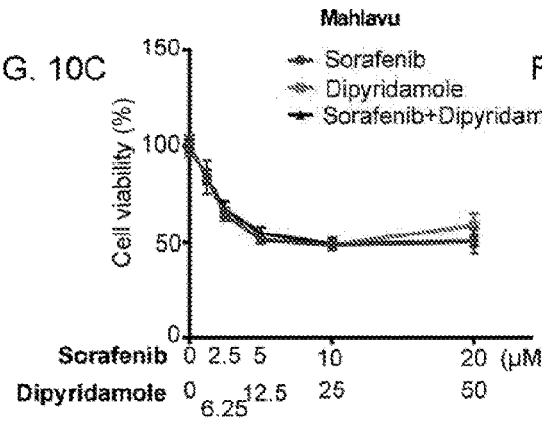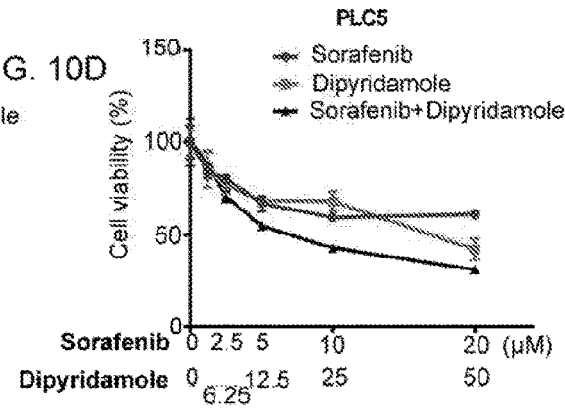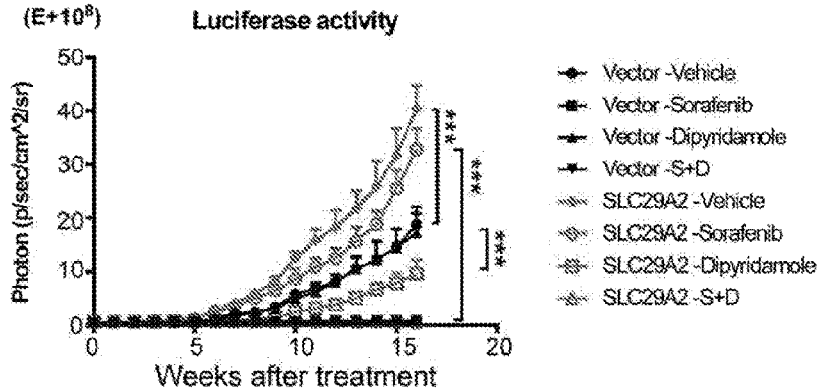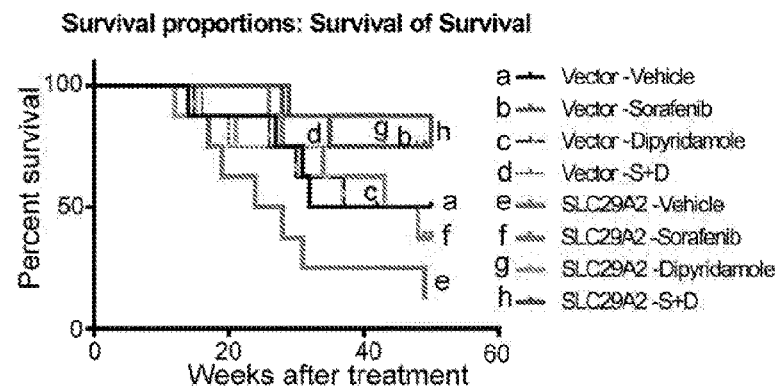

DIPYRIDAMOLE FOR USE IN TREATING SLC29A2 NUCLEAR-EXPRESSING CANCER

REFERENCE TO RELATED APPLICATION

This application is a national stage application (under 35 U.S.C. 371) of PCT/US2017/067294 filed on 19 Dec. 2017. which claims priority to U.S. provisional application 62/437,666 filed on 22 Dec. 2016, all of which are herein incorporated by reference in their entireties.

FIELD OF THE INVENTION

The present invention relates generally to anti-cancer therapy, more specifically to treatment of SLC29A2 nuclear-expressing cancer cells.

BACKGROUND OF THE INVENTION

Hepatocellular carcinoma (HCC) is the sixth common cancer and second most prevalent cause of death in cancer worldwide, and there are more than 45% of patients are diagnosed as late-stage HCC. Besides, according to BCLC staging and treatment guideline, sorafenib is the only treatment for late-stage HCC. However, patients who received sorafenib also get severe side effects, and only prolonged 3~6 months in overall survival. Therefore, it is urge to develop more effective and tolerance treatment.

SUMMARY OF THE INVENTION

In one aspect, the invention relates to use of a pharmaceutical composition comprising: (i) a therapeutically effective amount of dipyridamole; and (ii) a pharmaceutically acceptable carrier, in the manufacture of a medicament for suppressing proliferation, occurrence, and metastasis of cancer cells overexpressing the oncogene SLC29A2 in a cancer patient, and/or prolonging cancer patient survival.

In one embodiment, prior to the use according to the invention the cancer patient is identified as a candidate for dipyridamole treatment provided that a population of the cancer cells, which are obtained from the patient, exhibits nuclear overexpression of SLC29A2 as compared with a control. In one embodiment, the overexpression of SLC29A2 in the cancer cells is detected by histochemical staining of the nucleus in a tumor section obtained from the cancer patient.

In another aspect, the invention relates to use of dipyridamole and use of soratenib in the manufacture of a medicament for suppressing proliferation, occurrence, and metastasis of cancer cells overexpressing the oncogene SLC29A2 in a cancer patient, and/or prolonging cancer patient survival.

In another aspect, the invention relates to use of a pharmaceutical composition comprising: (i) a therapeutically effective amount of an inhibitor of the oncogene SLC29A2; and (ii) a pharmaceutically acceptable carrier, in the manufacture of a medicament for suppressing proliferation, occurrence, and metastasis of cancer cells overexpressing the oncogene SLC29A2 in a cancer patient, and/or prolonging cancer patient survival.

In one embodiment of the invention, the inhibitor of the oncogene SLC29A2 is at least one selected from the group consisting of dipyridamole, dilazep, draflzine, nitorbenzyl-thioinosine, and the derivatives thereof.

In another embodiment of the invention., the inhibitor of the oncogene SLC29A2 is selected from the group consisting of dipyridamole, SLC29A2 anti-sense small interfering RNA (siRNA), and an anti-SLC29A2 short hairpin RNA (shRNA), and anti-SLC29A2 neutralizing antibody.

In another embodiment of the invention, the cancer cells are at least one selected from the group consisting of liver cancer cells, breast cancer cells, head and neck cancer cells, and ovarian cancer cells.

In another embodiment of the invention, the cancer cells are liver cancer cells and contain a population that shows resistance to sorafenib treatment.

In another embodiment of the invention, according to the use of the invention the composition further comprises sorafenib.

In another embodiment of the invention, the use of the invention is in combination with simultaneous use of sorafenib in the manufacture of a medicament for suppressing proliferation, occurrence, and metastasis of cancer cells in a cancer patient, and, or prolonging cancer patient survival.

Alternatively, the invention relates to a pharmaceutical composition comprising: (i) a therapeutically effective amount of dipyridamole; and (ii) a pharmaceutically acceptable carrier, for use in suppressing proliferation, occurrence, and metastasis of cancer cells overexpressing the oncogene SLC29A2 in a cancer patient, and/or prolonging cancer patient survival.

In one embodiment, the pharmaceutical composition for use according to the invention further comprises an additional pharmaceutical composition comprising a therapeutically effective amount of sorafenib and a pharmaceutically acceptable carrier for use in suppressing, proliferation, occurrence, and metastasis of cancer cells in a cancer patient, and/or prolonging cancer patient survival.

The invention further relates to dipyridamole and sorafenib for use in suppressing proliferation, occurrence, and metastasis of cancer cells overexpressing the oncogene SLC29A2 in a cancer patient, and/or prolonging cancer patient survival.

The invention additionally relates a pharmaceutical composition comprising: (i) a therapeutically effective amount of an inhibitor of the oncogene SLC29A2; and (ii) a pharmaceutically acceptable carrier, for use in suppressing proliferation, occurrence, and metastasis of cancer cells overexpressing the oncogene SLC29A2 in a cancer patient, and/or prolonging cancer patient survival.

The invention further relates to a method for suppressing proliferation, occurrence, and metastasis of cancer cells overexpressing the oncogene SLC29A2 in a cancer patient, and/or prolonging cancer patient survival, the method comprising: administering to the cancer patient in need thereof a pharmaceutical composition comprising: (i) a therapeutically effective amount of dipyridamole; and (ii) a pharmaceutically acceptable carrier. The method may further comprise administering a therapeutically effective amount of sorafenib to the cancer patient in need thereof. In one embodiment, the dipyridamole and sorafenib are simultaneously administered to the cancer patient in need thereof.

The invention additionally relates a method for suppressing proliferation, occurrence, and metastasis of cancer cells overexpressing the oncogene SLC29A2 in a cancer patient, and/or prolonging cancer patient survival, the method comprising: administering to the cancer patient in need thereof a pharmaceutical composition comprising: (i) a therapeutically effective amount of an inhibitor of the oncogene SLC29A2; and (ii) a pharmaceutically acceptable carrier.

In one embodiment, prior to the administering step further comprising: (a) detecting nuclear expression of SLC29A2 in the cancer cells obtained from the cancer patient and comparing with a control; and (b) identifying the cancer patient as a candidate for dipyridamole treatment provided that a population of the cancer cells is detected to have nuclear-overexpression of SLC29A2 as compared with the control. The detecting step may be performed with an antibody against SLC29A2. The antibody detects nuclear overexpression of SLC29A2 in the cancer cells. The detecting step is performed by histochemical staining of the nucleus in a tumor section obtained from the cancer patient. In one embodiment, the method may further comprise administering a therapeutically effective amount of sorafenib to the cancer patient in need thereof. In one embodiment, the dipyridamole and sorafenib are simultaneously administered to the cancer patient. In one embodiment, the cancer patient has liver cancer cells with a population of the cancer cells exhibiting nuclear-overexpression of the oncogene SLC29A2.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1A-I shows SLC29A2 is an oncogene. (A) The SLC29A2 shown higher expression in forty-two tumor sections compared to their normal liver in TCGA dataset. (B,C) Immunohistochemistry staining indicates that the expression of SLC29A2 increases along with grade, and shows higher in lymph node metastasis and distant metastasis. (D) Cell number are assayed by Alamar blue, and the results show ectopic-expressed SLC29A2 in HCC cell lines increase cell proliferation. The results are triplicated and are represented by mean±SD. (E) Anchorage independent growth assay of SK-hep1 cells in soft agar demonstrate that SLC29A2 increase colony numbers. Images of foci are represented, and the bar chart is represented three independent assays of six wells. (F) SLC29A2 also increases trans-well migration in HCC cell lines. Images of Boyden chambers are shown, and the bar chart represented by mean±SD. (G) Western blot analysis of epithelial-mesenchymal transition markers shows that SLC29A2 promote mesenchymal markers and down-regulate epithelial markers. (H) Ectopic expression of SLC29A2 promotes sphere formation in SK-hep1 cells, bar chart is represented by mean±SD, triplicated assay. (I) SLC29A2 promotes tumor burden in the orthotopic liver models. The mock mice were injected with luciferase-carrying SK-hep1 cells. The SLC29A2 mice were injected with SLC29A2 ectopically expressing SK-hep1 cells. Images represent the tumor progression of one mice in each group along with time by IVIS system.

FIG. 2A-I shows that the oncogenic effects of SLC29A2 is STAT3-dependent. (A) Screening by protein kinase array indicates that SLC29A2 promote STAT3 phosphorylation. (B) The expressions of SLC29A2 and phospho-STAT3 in HCC patient tissues show positive correlation. n=234. (C) Expressing SLC29A2 in HCC cell lines promotes STAT3 phosphorylation and upstream kinase (Jak2 and Tyk2) activation. (D) Structural schematic of STAT3D, which is dominant-negative in DNA binding domain. (E) Introducing STAT3D can reduce SLC29A2-induced STAT3 phosphotylation. (F, G, H, I) Inhibiting STAT3 signaling reverses the SLC29A2-driven tumorigenic phenotypes, including proliferation (F), migration (C), anchorage-independent growth ability (H), and sphere formation (I).

FIG. 6A-E shows that combination of dipyridamole and sorafenib can enhance the inhibition effects in vitro and in vivo. (A) Combined treatment of dipyridamole and sorafenib enhance the reduction of cell viability especially the SLC29A2-expressing cells. (B) Combination of dipyridamole and sorafenib further reduced the SLC29A2-induced Stat3 phosphorylation. (C) The scheme of experimental design for in vivo treatment. (D) The tumor burden was measured at 6 weeks after treatment by IVIS system. (E) The combination treatment enhance the mice overall survival compared to single treatment and vehicle.

FIG. 8 is a Table showing SLC29A2 is amplified in different cancer cell lines,

FIGS. 10A-J show the effects of dipyridamole on SLC29A2-expressing cancer cells. (A, B, C, D) Combination of dipyridamole and sorafenib further decreased cell viabilities of HCC cell line, especially in SLC29A2 highly-expressed cells (B, D). (E) Treating dipyridamole decreased tumor progression in SLC29A2-expressed liver orthotopic model. Combination of dipyridamole and sorafenib could further decrease tumor progression. (F) Combination of dipyridamole and sorafenib further increased the mouse survival. (G, H, I) Treatment of dipyridamole decreased the nodules in primary liver (H) and metastatic lung (I). Combination of dipyridamole and sorafenib could further decrease nodules in the liver (H) and lung (I). There is no significant body weight changes and toxicity to mice under treatments of dipyridamole and/or sorafenib (J).

DETAILED DESCRIPTION OF THE INVENTION

Figure 3A:
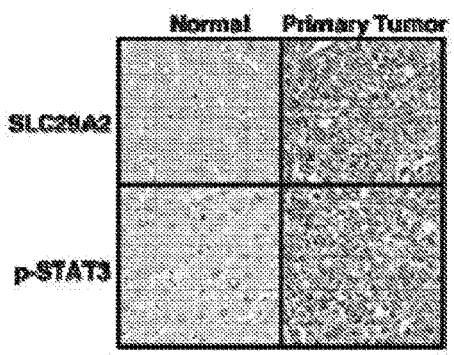
FIG. 3A-F shows that the aberrant nuclear expression of SLC29A2 contributes to the oncogenic effects. (A) Immunohistochemical staining of HCC tissues show that the aberrant nuclear expression of SLC29A2 and phosphorylated-STAT3 in primary tumor compared to adjacent normal tissue. (B) Ectopic expression of SLC29A2 increase the aberrant expression in nuclear. α-tubulin, pan Cadherin, and SP1 represent the marker of subcellular fractions. (C) Immunofluorescent staining of SK-hep1 cells shows that inhibition of nucleus pore by dominant-negative Ran-GTPase (Ran-Q69L) reduces the nuclear translocation of SLC29A2. Bar chart represents the distribution of SLC29A2 in Ran-WT and Ran-Q69L groups, n=300, (D, F) Inhibition of nuclear translocation reduced the SLC92A2-mediated tumorigenic phenotypes including proliferation (D) and migration (E). (F) Subcellular fractionation followed by immunoprecipitation indicates that SLC29A2 interact with STAT3 in nucleus.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term the scope and meaning of a term is the same, in the same context, whether or not it is highlighted. It will be appreciated that same thing can be said in more than one way. Consequently, alternative language and synonyms may be used for any one or inure of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which, this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "control" shall generally mean a normal counterpart cell.

The terms "cancer-initiating cells", "tumor-initiating cells", "cancer-initiating cells" are interchangeable.

The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on, results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$HED = \text{animal dose in mg/kg} \times (\text{animal weight in kg/human weight in kg})_{0.33}.$$

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Patient Tissue Samples and Immunohistochemical Staining

Human live cancer tissue arrays were purchased from SuperBio Chips (#CSA3) and BioMax (#LV208. and #LV2081). The tissue arrays were incubated in Dewax and HIER buffer H for dewax and antigen retrieval (#TA~100~DHBH, Thermo) at 95° C. for 15 minutes. The sections were then incubated with 3% hydrogen peroxide to remove endogenous peroxidase activities. After blocking with 10% goat serum, the sections were incubated with primary antibodies specific to SLC29A2 (1:1000 dilution, #ab48595, abeam) and phospho-STAB3 (1:1000 dilution,

9145, Cell Signaling Technology) in the blocking solution at 4° C. overnight. A dual-link HRP system (#k4065, Dako) was applied to conjugate primary antibodies and to develop color according to the instruction manual. The sections were then counterstained with hematoxylin. The expression of SLC29A2 and phosphor-STAF3 were evaluated by a pathologist using, a four-tier grading system (negative; 0, weakly positive: +1, moderately positive: +2, and strongly positive: +3) and the percentage of staining in each section. Nuclear expression of SLC29A2 scored in excess of +2 indicates over-expression.

Cell Lines

HCC cell lines (Sk-hep1 and Mahlavu) were maintained in Dulbecco's modified Eagle's medium (DMEM) with 10% fetal bovine serum, 1% non-essential amino acid, 1% L-glutamine, and 1% penicillin/streptomycin. All cells were tested for mycoplasma contamination.

Plasmids and Transfection pcDNA3.0/HA~SLC29A2 was generated according to Chen et al. (2010) (*Hepatologs*, 52(5), 1690-1701), To stably express SLC29A2 or STAT3D, HCC cell lines were transfected with the plasmid according to the instruction manual by JetPrime transfection reagent (Polyplus), and further selected in the presence of G418 (SK-hep1: 800 µg/mL, Mahlavu: 500 µg/mL)

Immunoprecipitation and Immunoblotting

Cells were lysed with a RIPA buffer containing protease inhibitor cocktail (#04693132001, Roche) and phosphatase inhibitor (#54625, Millipore), and equal amounts of lysate (20 µg/lane) were loaded onto a SDS-PAGE and blotted onto PVDF membranes. Western blotting was performed by using primary antibodies directed against SLC29A2 (#ab46595, abcam) or HA-tag (#MMS-101R, Covance), p-STAT3 (#9145, Cell Signaling Technology), STAT3 (#9139, Cell Signaling Technology). snail (#3879, Cell Signaling Technology), slug (#9585. Cell Signaling Technology), twist (#46702. Cell Signaling Technology), E-cadherin (#3195, Cell Signaling Technology). γ-catenin (#2309, Cell Signaling Technology), N-cadherin (#13116, Cell Signaling Technology), vimentin (#5741, Cell Signaling Technology), α-SMA (#se-53142, Santa Cruz), GAPDH (#GTX100118, GeneTex), survivin (#2808, Cell Signaling Technology), cyclin D1 (#2978, Cell Signaling Technology), p-Jak2 (#3771, Cell Signaling Technology), Jak (#3230, Cell Signaling Technology), p-Tyk2 (#9321, Cell Signaling Technology), Tyk2 (#9312, Cell Signaling Technology), Flag-tag (F1804, Sigma-Aldrich), α-tubulin (sc-8035, Santa Cruz)). pan Cadherin (#4068, Cell Signaling Technology), SPI (se-420, Santa Cruz), and β-actin (#MAB1501, Millipore).

For immunoprecipitation, indicated antibody was first incubated with protein A/G-conjugated magnet heads (protein A: #28-9513-78, protein (G: #28-9513-79, GE healthcare) for 1 hour at 4° C., and equal amounts of cell lysates were subsequently reacted with antibody-conjugated beads at 4° C. overnight. The pull-down heads were washed, eluted, and subsequently subjected to Western blotting for protein detection.

Soft Agar Anchorage-Independent Assay

The basal layer containing complete medium and 0.5% agarose was paved in 6-well plate (2 mL/well), and the top layer containing complete medium, 0.3% agarose, and a total of $1\times10^4$ cells was plated onto the basal layer (2 mL/well). Complete medium (2 mL) was added into each well and replaced every 3 days. After 3 weeks' incubation, colonies were stained with 0.3% crystal violet solution, and counted by image software.

Cell Proliferation and Cell Viability Assay

The cell proliferation and cell viability were detected by ALARMA BLUE® reagent (DAL1100, Thermo Fisher) according to the manufacturer's instruction. For cell proliferation assay, a total of $1.25\times10^3$ cells were seeded in 96-well plateAfter indicated incubation time, the medium was replaced with 10% ALARMA BLUE® for incubation at 37° C. for 1 hour. The ALAMAR BLUB® fluorescence was excited at 560 nm and measured at 590 nm.

Migration Assay

A total of $1\times10^4$ cells were seeded in the upper chamber of 8 micron Boyden chamber insert (#MCEP24H48, Millipore) containing a serum-free medium. The inserts were then hanged on the 24-well plate containing a complete medium. After 16 hours, the non-migrated cells were wiped out and the migrated cells were fixed with methanol and stained with Liu's stain. The migrated cells were counted by ImageJ software.

Sphere Formation Assay

A total of $1\times10^4$ cells were seeded in the ultra-low attachment 6-well plate (#3471, Corning) containing DMEM/F12 medium, FGF (20 ng/mL), bFGF (20 ng/mL), B27, and insulin (4 µg/mL). The spheres were passaged every 5~8 days until they reached a diameter of 100 µm and counted under phase contrast microscopy before they passaged.

Cellular Fractionation

Cells were harvested and fractionated into cytosolic, membrane, and nuclear fractions with Cellular Fractionation kit (#78840, Thermo Scientific) according to the manufacturer's instruction. The same amount of cytosolic, membrane, and nuclear fractions was used for immunoprecipitation and immunoblotting. Alpha-tubulin, pan cadherin, and SP1 were served as controls for cellular fractionation and immunoblot loading.

Confocal Microscopy Analysis

Cells were grown on glass slides. After washing with ice-cold PBS, cells were fixed with methanol, blocked with 5% BSA, and incubated with primary antibodies at 4° C. overnight. The slides were washed with PBS, and incubated with Alexa488 or AIexa594-conjugated secondary antibodies. The slides were then washed with PBS, stained with DAPI and mounted with Dako fluorescent mounting medium (#S3025, Dako). The immunostained cells were acquired by Zeiss LSM 700 laser-scanning microscope with 63X/1.4 objective. The images were analyzed with ZEN, AxioVision, and imagesJ software.

Site-Directed Mutagenesis

The SLC29A2-N48D and SLC29A2-N57D were generated by site-directed mutagenesis QuikChange II Site-Directed Mutagenesis Kit (#200523, Agilent) following the instruction manual. The primers were as follows: SLC29A2-N48D: CCGGGGCCGGCGACAGCACAGCC (SEQ ID NO: 1; forward), GGCTGTGCTGTCGCCGGCCCCGG (SEQ ID NO: 2; reverse), and SLC29A2-N57D: GATCCTGAGCACCGACCACACGGGTCC (SEQ ID NO: 3; forward). GGACCCGTGTGGTCGGTGGTCAGGATC (SEQ ID NO: 4; reverse). The sequences were confirmed by DNA sequencing.

Mouse Orthotopic Model

All animal procedures were conducted under the approval of the institutional animal care and user committee of Academia Sinica. The luciferase-carrying SK-hep1 cells ($1\times10^6$ cells each mice) were mixed with matrigel (#354262, BD) injected into the liver of male nude mice at the 6-8 weeks of ages. Mice were anesthetized with isoflurane and i.p. injected with 50 µL D-luciferin (#XR-1001, Xenogen), followed by detecting the luciferase activities using the IVIS Image system after 4-week injection. The luciferase activity-positive mice were random divided into groups, and gavaged orally with vehicle, sorafenib, dipyridamole or combined treatment once a day (sorafenib: 10 mg/kg/day, dipyridamole: 25 mg/kg/day, dissolved in Kolliphor EL/ethanol, 50%:50% at 4× concentration). The luciferase activities were detected by the IVIS Image system every two weeks, and the images were analyzed with IVIS operating software.

The mice wore sacrificed 48 weeks after the tumor injection or before the tumors grew larger than allowed. The tumor samples were collected and fixed with 4% paraformaldehyde.

Bioioformaties Analysis

GSE14520-GPL3921 was collected from Gene Expression Omnibus, and there were 214 paired HCC patients in this dataset. Level 3 of RNAseq data of 46 paired HCC patients were collected from TCGA. All these data were analyzed by student's t test.

Statistical Analyses

Except when indicated, each sample was assayed in triplicate. For in vitro analysis, each experiment was repeated at least three times. All error bars represent standard deviation. Student's t test was applied to compare two groups of independent sample. Correlations were analyzed by Pearson correlation. P values<0.05 were considered as statistically significant Results SLC29A2 was Amplified and Highly Expressed in Different Cancer Types It was discovered that SLC29A2 was amplified in HCC tissue and cell lines. Here, we have emphasized the importance of SLC29A2 in different cancer types by in silico investigation. By using the cBioportal database, we found that SLC29A2 is also amplified in other types of cancer, including breast cancer, pancreatic cancer, head and neck cancer, and ovarian cancer. Analyzing the CCLE dataset by in-house protocol or eBioportal database showed the SLC29A2 was amplified in different cell lines (FIG. 8, Table 1). By using the FireBrowse database, the expression of SLC29A2 in different cancer tissues was higher than their normal tissues in TCGA dataset. These results indicated that the amplification and aberrant expression of SLC29A2 was not only in HCC, but also in other cancer types.

SLC29A2 was an Oncogene in HCC

Figure 9A:
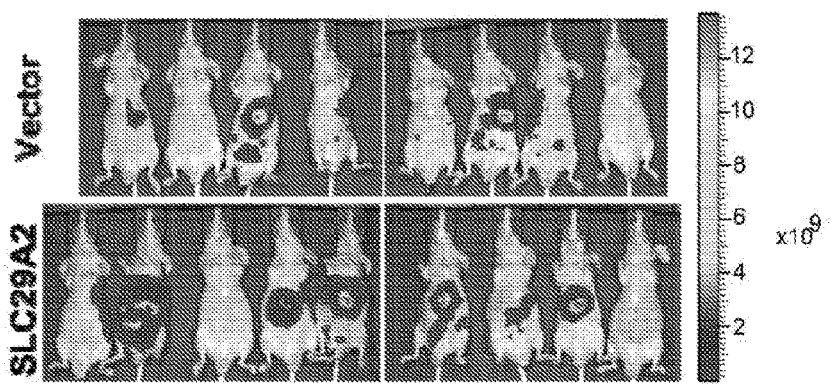
FIGS. 9A-F show the effect of SLC29A2 expression in the tumor mouse model. (A B) Ectopic expression of SLC29A2 promoted tumor progression in the liver orthotopic tumor model. (C) SLC29A2 decreased mouse survival. (D, E, F) Ectopic expression of SLC29A2 increased nodules in the primary liver (E) and metastatic lung (F).
Figure 9B:
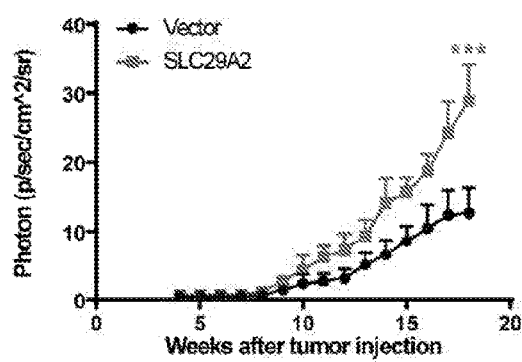
Figure 9C:
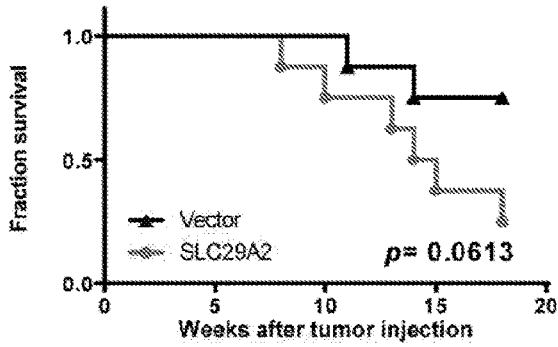
Figure 9D:
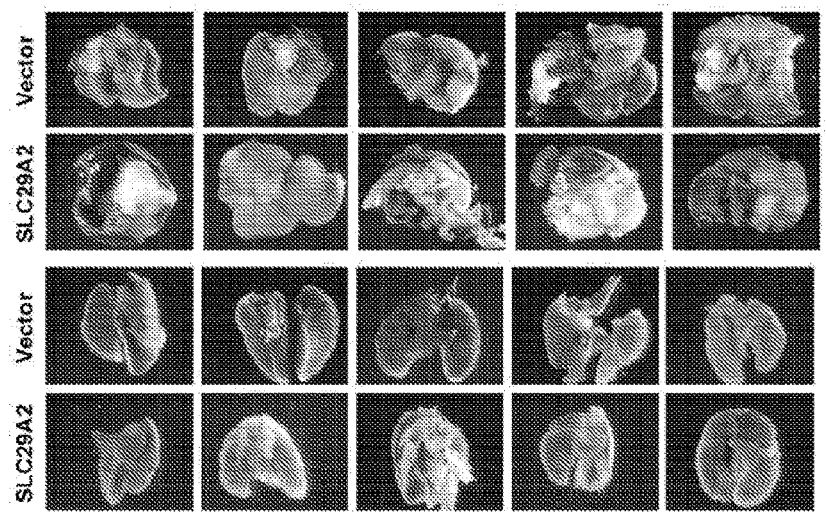
Figure 9E:
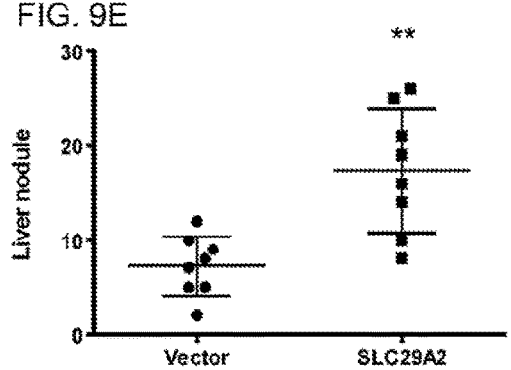
Figure 9F:
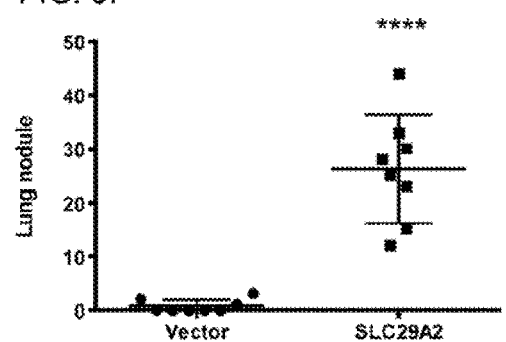
Figure 10G:
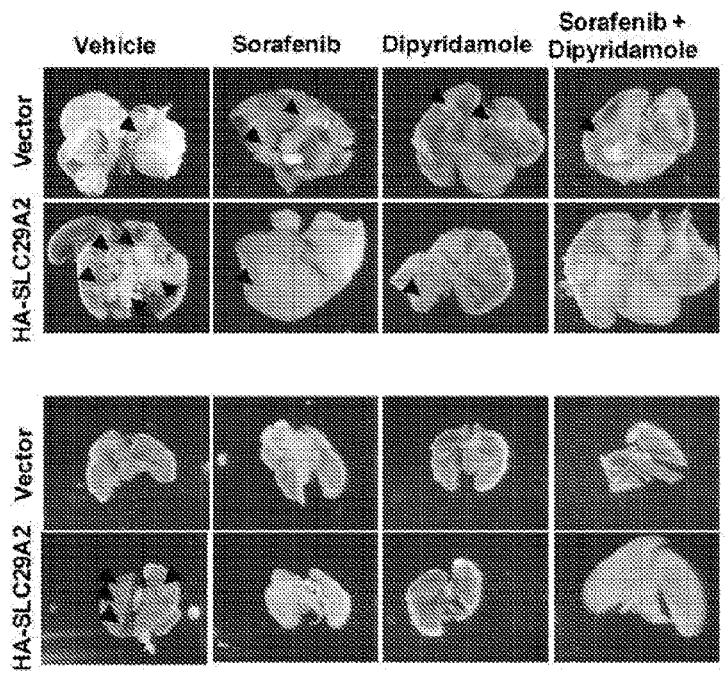
Figure 10H:
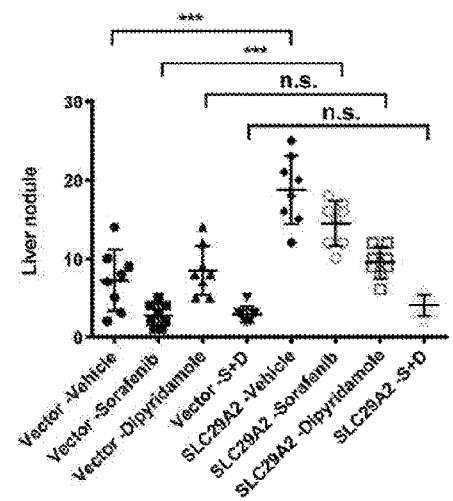
Figure 10I:
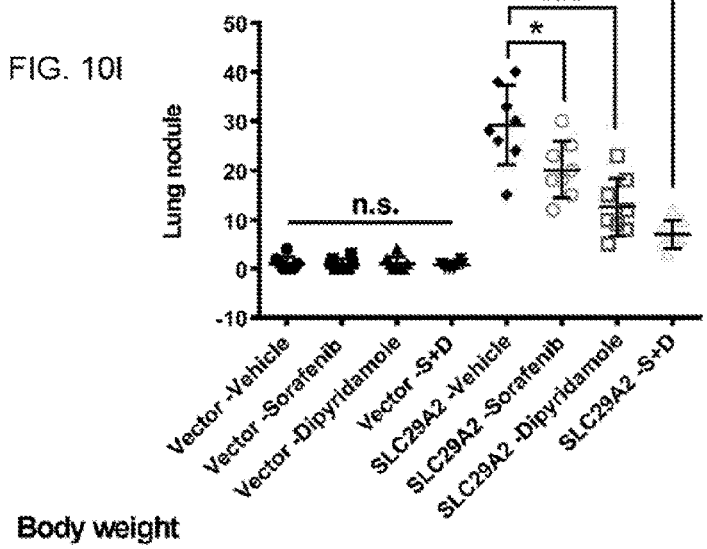
Figure 10J:
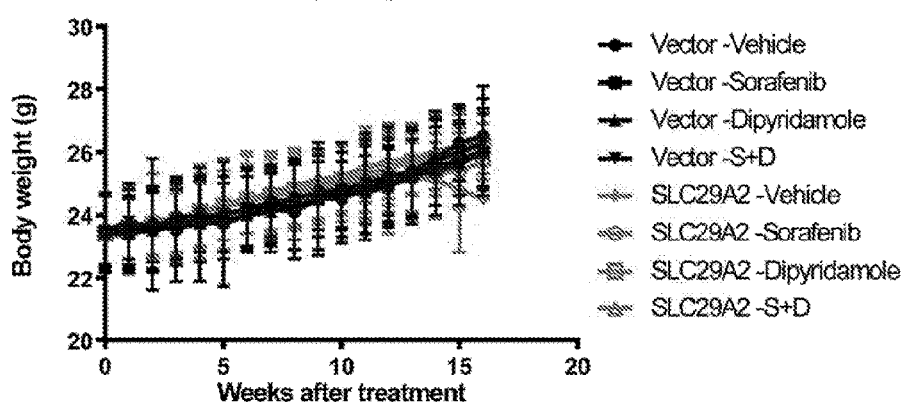

As we took HCC as a model to investigate the oncogenic properties of SLC29A2, we first in silico investigated the SLC29A2 expression in HCC sample. The results showed that SLC29A2 had higher expression in HCC tumors than normal tissues in TCGA dataset (FIG. 1A). The immunohistochemical staining also showed that the expression of SLC29A2 increased during tumor progression (FIGS. 1B, and 1C upper panel). The expression of SLC29A2 increased in lymph node metastatic and distant metastatic tissues compared to primary tumors (FIG. 1C, lower panel). To investigate whether SLC29A2 is an oncogene in HCC, we ectopically expressed SLC29A2 in HCC cell lines. The functional studies showed that SLC29A2 promoted proliferation (FIG. 1D), anchorage-independent growth (AIG) ability (FIG. 1E) and trans-well migration (FIG. 1F) in the HCC cell lines SK-hep1 and Mahlavu. Analyzing the expression of several markers indicated that SLC29A2 promoted epithelial-mesenchymal transition (EMT) phenotypes (FIG. 1G). SLC29A2 also promoted cancer-initiating-cell properties in HCC (FIG. 1H). We conducted orthotopic tumor mouse model in nude mice, and the results also showed that SLC29A2 promoted tumor progression and metastasis in vivo (FIG. 1I). Ectopic expression of SLC29A2 promoted tumor progression in the liver orthotopic tumor model (FIG. 9A-B). SLC29A2 decreased mouse survival (FIG. 9C). FIGS. 9D-F show that ectopic expression of SLC29A2 increased nodules in the primary liver (FIG. 9E) and metastatic lung (9F). From these results and the previous studies, we found that SLC29A2 was not only essential, but also sufficient in tumorigenicity, including proliferation, AIG, migration, and tumor progression in the xenograft model.

The Oneogenie Properties of SLC29A2 were Through Stat3 Activation

To investigate the underlying mechanism of SLC29A2-induced oncogenic effects, we conducted protein kinase array to investigate the pathway that might be involved. The results showed that expressing SLC29A2 in HCC cell lines increased. Stat3 phosphorylation (FIG. 2A). The immunohistochemical staining also showed that the expression of SLC29A2 was positively correlated with phosphorylated Stat3 in HCC tissue samples (FIG. 2B). Ectopic expression of SLC29A2 in HCC cell lines also showed increased Stat3 phosphorylation and upstream activator Jak2 and Tyk2 (FIG. 2C). One downstream signaling factor survivin was activated, but another factor eyelin D1 was down-regulated surprisingly (FIG. 2C). To elucidate the importance of Stat, we took the advantage of Stat3D, which was a dominant-negative Stlit3 mutated in DNA-binding domain (FIG. 2D). The results showed that co-expressing Stat3D decreased SLC29A2-induced Stat3 phosphorylation and reversed the cyclin D1 down-regulation (FIG. 2E). Functional studies also showed that co-expression of Stat3D reversed SLC29A2-induced oncogenic effects, including proliferation (FIG. 2F), migration (FIG. 2G), AIG ability (FIG. 2H), and sphere formation (FIG. 2I). These results indicated that SLC29A2-mediated oncogenic effects were Stat3-dependent.

Figure 3B:
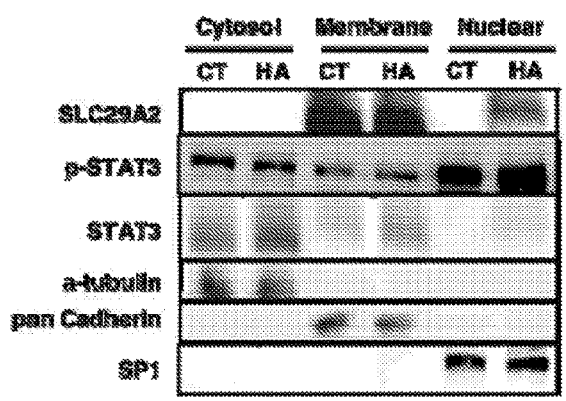
Figure 3C:
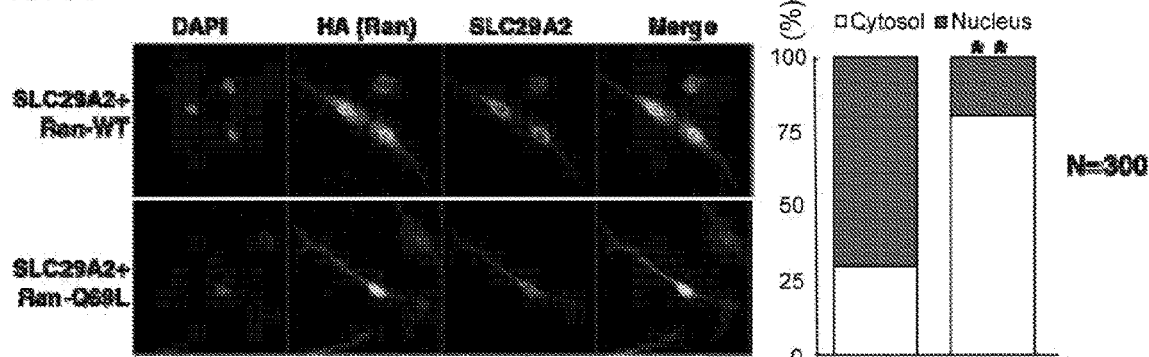
Figure 3D:
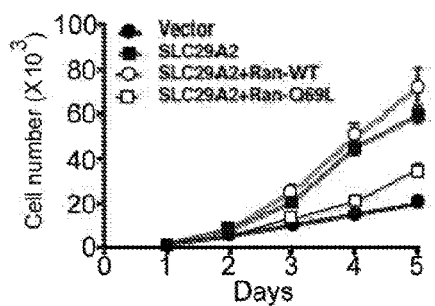
Figure 3E:
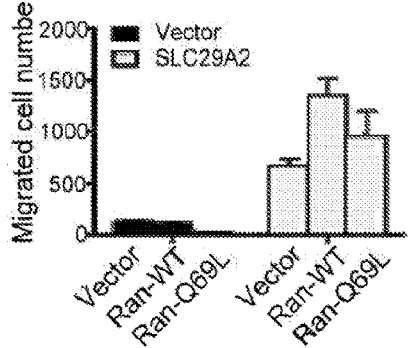
Figure 3F:
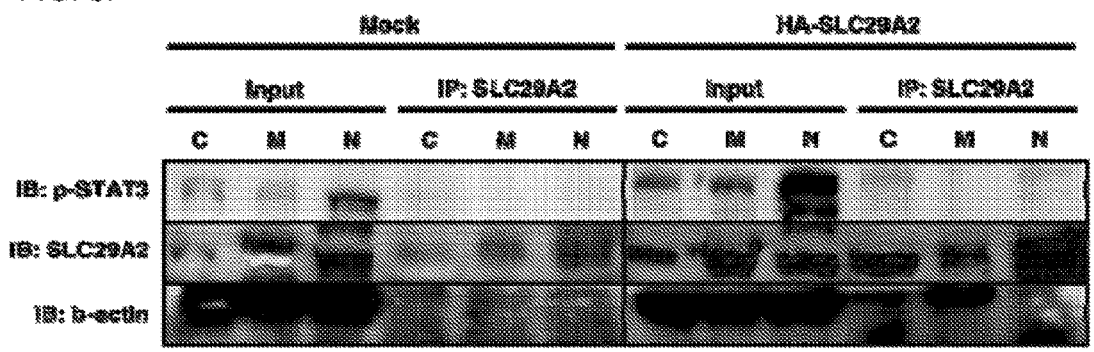

The Aberrant Nuclear Expression of SLC29A2 Contributed to the Oncogenic Properties and Stat3 Phosphorylation The results of immunohistochemical staining showed that SLC9A2 aberrantly expressed in the nucleus in the HCC tissues as compared to the adjacent normal tissues FIG. 3A). We confirmed the nuclear expression by subcellular fractionation, and found that SLC29A2-ectopically expressing cells showed increased SLC29A2 expression in the nuclear fraction, while the control group only expressed SLC29A2 in the membrane fraction (FIG. 3B). The phosphorylated Stat3 (p-STAT3) also increased in the nuclear fraction as compared to the control group, which was concordant with the results in immunohistochemical staining (FIG. 3A-B). To confirm that the aberrant nuclear expression indeed translocated from the membrane, we expressed the wild type and dominant-negative Ran-GTPase (Ran-Q69L) in the cells, which control the cargo transport of nuclear pore. The confocal microscopy showed that expressing Ran-Q69L could decrease the nuclear translocation of SLC29A2 (FIG. 3C). Functional studies also showed that blockage of the nuclear translocation of SLC29A2 reduced the proliferation (FIG. 3D) and trans-well migration (FIG. 3E) of HCC cells. Furthermore, we found that SLC29A2 could interact with Stat3 by immunoprecipitatiort (FIG. 3F), and the interaction was mainly in the nucleus. These results demonstrated that the nuclear translocation of SLC29A2 contributed to the oncogenic effects by interacting with Stat3 and promoting Stat3 translocation.

Figure 4A:
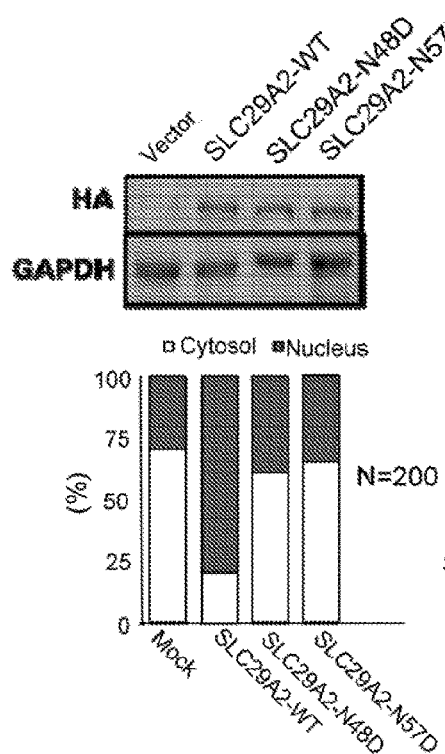
FIG. 4A-E shows that the glycosylation modifications of SLC29A2 lead to membrane anchorage and nuclear translocation. (A) Western blotting shows the ectopic expression of glycosylation mutants (N48D and (N57D) of SLC29A2. (B) Immunofluorescence confocal microscopy indicates the glycosylation modification of SLC29A2 is essential for nuclear translocation and p-Stat3 activation. (C, D) Functional assay indicate that the glycosylation modifications are essential for SLC29A2-mediated proliferation (C) and transwell migration (D). (E) Mutated of glycosylation sites also reverse the SLC29A2-driven epithelial-mesenchymal transition phenotype.
Figure 4B:
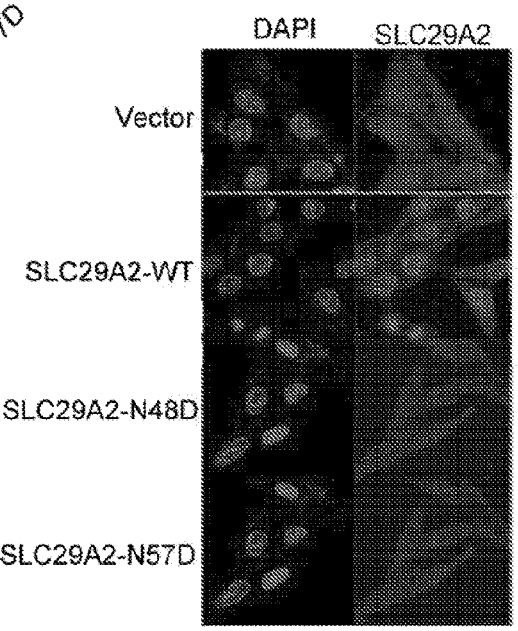
Figure 4C:
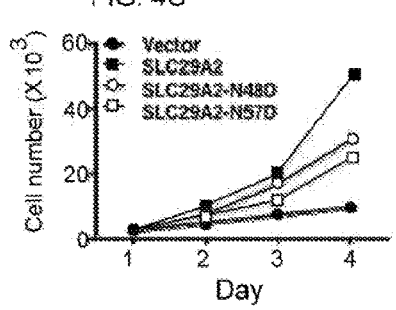
Figure 4D:
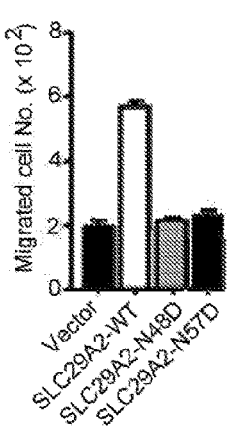
Figure 4E:
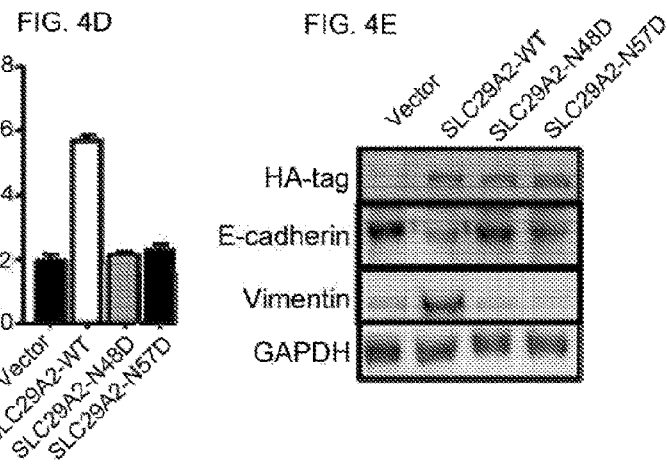

Glycosylation Modification of SLC29A2 is Essential for Membrane Anchorage and Tumorigenicity There are two N-glycosylation modification sites in SLC29A2, residue 48 and residue 57, and these modifications are important in membrane anchorage after the proteins had been translated. We investigated whether these modifications would also contribute to SLC29A2 nuclear translocation. After generating and expressing glycosylation site mutants (N48D and N57D, FIG. 4A), we found that the nuclear translocation of SLC29A2 decreased when disrupting the membrane anchorage (FIG. 4B). Ectopic expression followed by doxycyclin treatment showed that the glycosylation mutant did not alter the protein stability of SLC29A2 (FIG. 4A-B). Functional assays showed that the proliferation (FIG. 4C) and migration (FIG. 4D) of glycosylation mutants decreased as compared to the wild type. And the EMT markers were reversed to the epithelial phenotype in the cells expressing the glycosylation mutants (FIG. 4E). These results indicated that the glycosylation modifications of SLC29A2 were important for membrane anchorage and nuclear translocation, which then contributed to oncogenic properties.

Inhibition of SLC29A2 Reduced the Oncogenic Phenotypes in SLC29A2-Nuclear Expressing Cells.

Figure 5A:
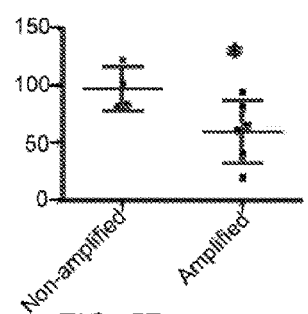
FIG. 5A-E shows that treatment of dipyridamole decreased the SLC29A2-driven oncogenic phenotype in aberrant-expressed cells. (A) The HCC cell lines carrying amplified SLC29A2 were sensitive to dipyridamole compared to non-amplified cells. The cell viability assay was conducted with ALAMAR BLUE®, and the Y-axis represents the IC50 of cells to dipyridamole. (B) SK-hep1 cells expressing SLC29A2 were sensitive to dipyridamole than control cells. (C) Dipyradamole reduced trans-well migration of SLC29A2-expressing cells. (D) The dipyridamole inhibits the SLC29A2-induced Stat3 phosphorylation and cyclin D1 down-regulation, (E) The confocal microscopy shows that dipyridamole reduces the nuclear translocation of SLC29A2. The left panel represents the percentage of the SLC29A2 expressing in the nucleus.
Figure 5B:
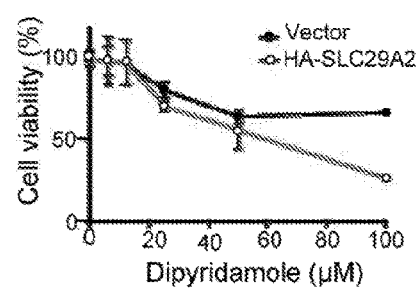
Figure 5C:
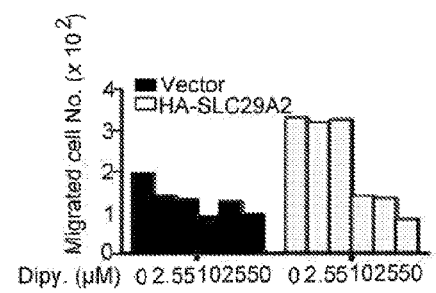
Figure 5D:
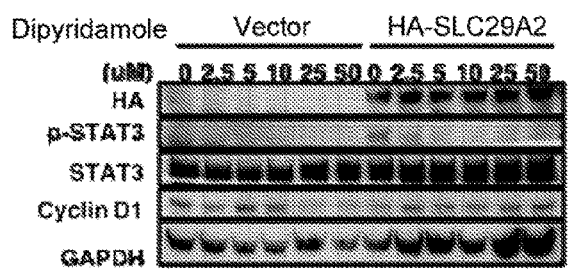
Figure 5E:
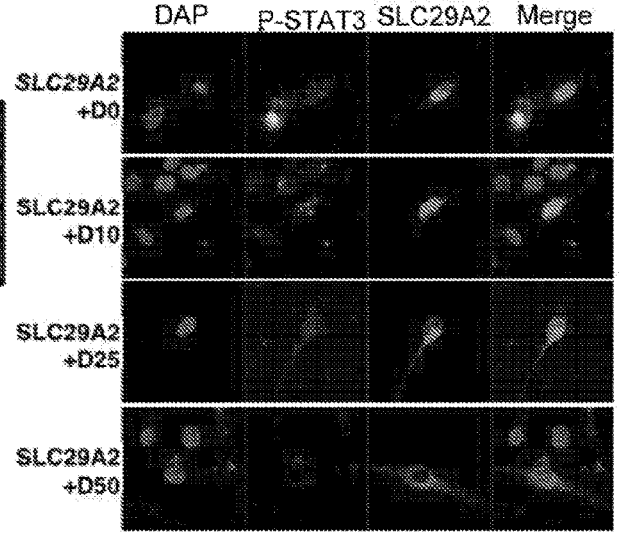

We discovered that SLC29A2 played an important role in HCC tumorigenesis. We then investigated whether SLC29A2 could be a therapeutic target. After treating the HCC cell lines with SLC29A2 inhibitor, we found that the SLC29A2-amplified cells were much more sensitive to the SLC29A2 inhibitor as compared to the non-amplified cells (FIG. 5A). SK-hep1 cells which ectopically expressing SLC29A2 were also much more sensitive than the control cells (FIG. 5B). Inhibiting SLC29A2 also decreased the migration ability of SLC29A2 ectopically expressing cells (FIG. 5C). Furthermore, we found that the SLC29A2 inhibitor treatment decreased SLC29A2-induced Stat3 phosphorylation in a dosage-dependent manner, and down-regulation of cyclin D1 was reversed (FIG. 5D). The results of confocal microscopy indicated that SLC29A2 inhibitor treatment also decreased SLC29A2 and Stat3 nuclear translocation (FIG. 5E). These results indicated that inhibiting SLC29A2 reduced the oncogenic phenotype in aberrantly expressing cells by reducing the nuclear translocation and Stat3 phosphorylation.

Combination Treatment with Sorafenib Enhanced the Anti-Tumor Effects of SLC29A2 Inhibitor.

Sorafenib is the only FDA-approved medicine to treat patients of late-stage HCC. However, we found that SLC292 expressing cell were much more resistant to sorafenib as compared to the control cells (FIG. 6A). To discover a new therapeutic strategy, we treated the cells with combined SLC29A2 inhibitor and sorafenib. The results showed that combination treatment further reduced the cell viabilities of both control and SLC29A2 ectopically expressing cells (FIG. 6A). We also found that combination treatment further decreased Stat3 phosphorylation in SLC29A2 ectopically expressing cells (FIG. 6B). To further investigate the therapeutic effect, we designed the orthotopic tumor mouse model to examine the effect of SLC29A2 inhibitor and its combination with sorafenib (FIG. 6C). Four weeks after being injected with the SK-hep1 cells carrying luciferase expression (Vehicle or HA-SLC29A2 transfected SK-hep1), the mice were gavage fed once a day with SLC29A2 inhibitor, sorafenib, or the combination treatment. The results showed that SLC29A2 promoted tumor progression in the orthotopic tumor mouse model, and treating sorafenib reduced the tumor burden in both SLC29A2-expressing and control groups (FIG. 6D). Treating with the SLC29A2 inhibitor dipyridamole decreased the tumor progression in SLC29A2-expressing group, which was concordant with the results in vitro (FIG. 6D). Combination treatment significantly decreased the tumor burden in both SLC29A2-expressing and control groups (FIG. 6D). In addition, combination treatment significantly increased the overall survival in SLC29A2-expressing and control group (FIG. 6E).

FIGS. 10A-D show that combination of dipyridamole and sorafenib further decreased cell viabilities of HCC cell lines, especially in SLC29A2 highly-expressed cells (10B, 10D). Treating dipyridatnole decreased tumor progression in SLC29A2-expressed liver orthotopic model (10E). Combination of dipyridamole and sorafenib could further decrease tumor progression. (10F) Combination of dipyridamole and sorafenib further increased the mouse survival. (FIGS. 10G, H. I. show that treatment of dipyridamole decreased the nodules in primary liver (10H) and metastatic lung (10I). Combination of dipyridamole and sorafenib could further decrease nodules in the liver (10H) and lung (10I). Mice treated with dipyridamole and/or sorafenib did not show significant body weight changes or toxicity (10J).

Figure 7:
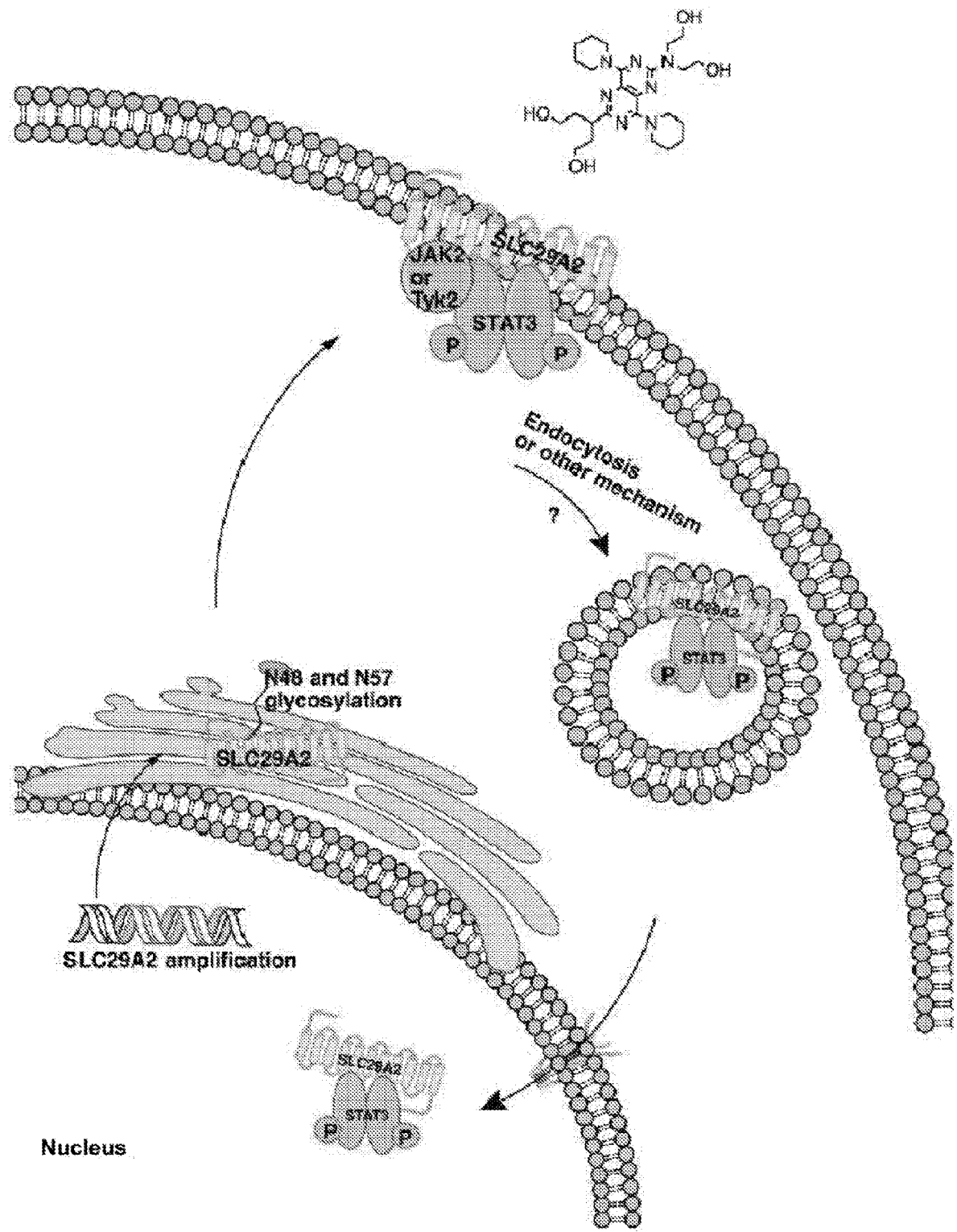
FIG. 7 illustrates a proposed model of the study.

In conclusion, we have discovered that SLC29A2 was a novel oncogene, and promoted HCC cells proliferation, AIG ability, migration, and cancer-initiating cell properties by interacting with phosphorylated Stat3 (FIG. 7). We found that not only the SLC29A2 amplification was correlated with the late-stage; the expression of SLC92A2 also increased in tumor progression (FIG. 1A-B). The public dataset also showed that SLC29A2 was amplified and highly expressed in other cancer types, including breast cancer, pancreatic cancer, and lung cancer. These results indicated that SLC29A2 played an important role in tumorigenesis of different tissues.

The expression SLC29A2 promoted Stat3 phosphorylation. Cyclin D1, a down-stream signaling factor, was down-regulated in. SLC29A2-expressing cells (FIG. 2C). Although many studies had showed that the expression of cyclin D1 increased during tumor progression (Yashiro et al (2007) *Cancer Science*, 98(5), 629-635), there were some studies indicated that the down-regulation of cyclin D1 was correlated with cancer metastasis (Mejlvang et al (2007) *Molecular Biology of the Cell*, 18(11), 4615-4624), stem cell properties (Matsui et al (2002) *The Journal of Biological Chemistry*, 277(39), 36167-36173), and poor survival outcome in patients (Lehn et al (2010) *The American Journal of Pathology*, 177(6), 2886-2897). These findings showed similar phenotypes in SLC29A2-expressing cells. We also found the down-regulation of cyclin D1 was caused by promoting cyclin D1 phosphorylation and increasing protein degradation (data not shown). These results indicated that SLC29A2 might have other mechanisms contributing to the late-stage cancer progression.

Our results indicated that the aberrant nuclear expression of SLC29A2, and the nuclear-expressing SLC29A2 contributed to the oncogenic phenotypes (FIG. 3). The glycosylation modification of SLC29A2 was not only important for membrane anchorage, but also important for oncogenic phenotypes (FIG. 4). Studies had shown that the glycosylated modification was important to membrane protein folding and function properly (Console et al (2015). *Biochimica Et Biophysica Acta*, 1853(7), 1636-1645). Our data suggested that the glycosylation mutant did not affect the protein stability of SLC29A2 (data no shown). The results also suggested that the interaction of SLC29A2 and Stat3 were mainly occurred in nucleus, indicating, a novel jak/Stat pathway that involved in tumor progression.

For the late-stage HCC patients, sorafenib is the only FDA-approved treatment. However, patients who received sorafenib suffered from severe side effects and spent million dollars to prolong overall survival only for 3~6 months. In this study, we found that inhibiting SLC29A2 significantly reduced the tumor progression especially in SLC29A2-expressing cells in vitro and in vivo. Our results also indicated that the combination of SLC29A2 inhibitor and sorafenib further enhanced the inhibitory effects (FIG. 6), suggesting that the patient might be able to reduce the dosage of sorafenib and lessen the side effects. Moreover, combination treatment prolonged the mouse overall survival as compared to single treatment. Since SLC29A2 was also amplified and highly expressed in other types of cancer, inhibiting SLC29A2 might be also effective to other cancer types. In summary, we discovered SLC29A2, a novel oncogene, could be a biomarker and therapeutic target in cancer.

In summary, overexpression of SLC29A2 showed correlations with poor differentiation and distant metastasis in HCC patients. Ectopic expression of SLC29A2 in HCC cell lines indicated that SLC29A2 promoted oncogenic properties, including proliferation, anchorage-independent growth epithelial-mesenchymal transition, cancer initiating cell features, and tumor progression in orthotopic HCC model. SLC29A2 overexpression promoted STAT3 phosphorylation and interacted with STAT3 to facilitate tumor progression. There was an increased nuclear expression of SLC29A2 in HCC cell lines and in tumor progression of HCC patient tissues. The interaction between SLC29A2 and STAT3 mainly occurred in nucleus. inhibition of nuclear transportation decreased the nuclear translocation of SLC29A2, its interaction with STAT3, and its oncogenic phenotypes. Inhibiting the glycosylation modification at amino acid residues 48 or 57 of SLC29A2 also decreased its nuclear translocation and oncogenic features, suggesting that the membrane anchorage of SLC29A2 is essential for its nuclear translocation. Finally, we showed that inhibition of SLC29A2 decreased the nuclear expression and tumor burden in vivo. The results indicate a novel role of overexpressed-SLC29A2 contributing to HCC tumor progression and SLC29A2 served as a new target for developing novel therapeutic and diagnostic strategies.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for suppressing proliferation, occurrence and metastasis of SLC29A2 nuclear-overexpressing cancer cells and/or prolonging cancer patient survival in a cancer patient having the SLC29A2 nuclear-overexpressing cancer cells, comprising:
   administering to the cancer patient having the SLC29A2 nuclear-overexpressing cancer cells, a pharmaceutical composition comprising:
   (i) a therapeutically effective amount of dipyridamole; and
   (ii) a pharmaceutically acceptable carrier,
   to suppress the proliferation, occurrence and metastasis of the SLC29A2 nuclear-overexpressing cancer cells and/or prolong the cancer patient survival in the cancer patient having the SLC2942 nuclear-overexpressing cancer cells,
   wherein the SLC29A2 nuclear-overexpressing cancer cells are at least one selected from the group consisting of liver cancer cells, breast cancer cells, pancreatic cancer cells, lung cancer cells, head and neck cancer cells, and ovarian cancer cells.

2. The method of claim 1, prior to the administering steps further comprising identifying the cancer patient as a candidate for dipyridamole treatment provided that a cell population in a cancer tissue sample obtained from the cancer patient exhibits nuclear overexpression of SLC29A2 as compared with a control obtained from an adjacent normal tissue.

3. The method of claim 1, wherein the cancer cells are liver cancer cells.

4. The method of claim 1, wherein the cancer cells are liver cancer cells which contain a population that shows resistance to sorafenib treatment.

5. The method of claim 1, further comprising administering a therapeutically effective amount of sorafenib to the cancer patient having the SLC29A2 nuclear-overexpressing cancer cells.

6. The method of claim 1, wherein the pharmaceutical composition further comprises sorafenib.

7. A method for suppressing proliferation, occurrence and metastasis of SLC29A2 nuclear-overexpressing cancer cells and/or prolonging cancer patient survival in a cancer patient having the SLC29A2 nuclear-overexpressing cancer cells, comprising:
   administering a pharmaceutical composition comprising:
   (i) a therapeutically effective amount of an inhibitor of the oncogene SLC29A2, the inhibitor of the oncogene SLC29A2 being at least one selected from the group consisting of dipyridamole, dilazep, draflzine and nitorbenzylthioinosine; and
   (ii) a pharmaceutically acceptable carrier,
   to the cancer patient to suppress the proliferation, occurrence and metastasis of the SLC29A2 nuclear-overexpressing cancer cells and/or prolong the cancer patient survival in the cancer patient having the SLC29A2 nuclear-overexpressing cancer cells, wherein the SLC29A2 nuclear-overexpressing cancer cells are at least one selected from the group consisting of liver cancer cells, breast cancer cells, pancreatic cancer cells, lung cancer cells, head and neck cancer cells, and ovarian cancer cells.

8. A method for suppressing proliferation, occurrence and metastasis of SLC29A2 nuclear-overexpressing cancer cells and/or prolonging cancer patient survival in a cancer patient having the SLC29A2 nuclear-overexpressing cancer cells, comprising:
   administering a therapeutically effective amount of an inhibitor of oncogene SLC29A2 and a therapeutically effective amount of sorafenib to the cancer patient having the SLC29A2 nuclear-overexpressing cancer cells to suppress the proliferation, occurrence and metastasis of the SLC29A2 nuclear-overexpressing cancer cells and/or to prolong the cancer patient survival in the cancer patient having the SLC29A2 nuclear-overexpressing cancer cells, wherein the inhibitor of the oncogene SLC29A2 is at least one selected from the group consisting of dipyridamole, dilazep, draflzine and nitorbenzylthioinosine, and further wherein the SLC29A2 nuclear-overexpressing cancer cells are at least one selected from the group consisting of liver cancer cells, breast cancer cells, pancreatic cancer cells, lung cancer cells, head and neck cancer cells, and ovarian cancer cells.

9. The method of claim 8, prior to the administering step further comprising identifying the cancer patient as a candidate for dipyridamole treatment providing that a cell population in a cancer tissue sample obtained from the cancer patient exhibits nuclear overexpression of SLC29A2 as compared with a control obtained from an adjacent normal tissue.

10. The method of claim 8, wherein the cancer cells are liver cancer cells.

11. The method of claim 8, wherein the cancer cells are liver cancer cells which contain a population that shows resistance to sorafenib treatment.

12. The method of claim 7, wherein the pharmaceutical composition further comprises sorafenib.

13. The method of claim 7, further comprising administering a therapeutically effective amount of sorafenib to the cancer patient having the SLC29A2 nuclear-overexpressing cancer cells.

14. The method of claim 7, to the administering step further comprising identifying the cancer patient as a candidate for dipyridamole treatment providing that a cell population in a cancer tissue sample obtained from the cancer patient exhibits overexpression of SLC29A2 as compared with a control obtained from an adjacent normal tissue.

15. The method of claim 7, wherein the cancer cells are liver cancer cells.

16. The method of claim 7, wherein the cancer cells are liver cancer cells which contain a population that shows resistance to sorafenib treatment.

17. The method of claim 13, wherein the dipyridamole and the sorafenib are administered simultaneously.

18. The method of claim 13, wherein the inhibitor of the oncogene SLC29A2 and the sorafenib are administered simultaneously.

19. The method of claim 5, wherein the dipyridamole and the sorafenib are administered simultaneously.

\* \* \* \* \*

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: SLC29A2-N48D Forward

<400> SEQUENCE: 1
ccggggccgg cgacagcaca gcc                                              23

<210> SEQ ID NO 2
<211> LENGTH: 23
<212> TYPE: DNA
<213> ORGANISM: Artificial Sequence
<220> FEATURE:
<223> OTHER INFORMATION: SLC29A2-N48D Reverse

<400> SEQUENCE: 2
ggctgtgctg tcgccggccc cgg                                              23

<210> SEQ ID NO 3
<211> LENGTH: 27
<212> TYPE: DNA
<213> ORGANISM: Artificial Sequence
<220> FEATURE:
<223> OTHER INFORMATION: SLC29A2-N57D Forward
```

```
<400> SEQUENCE: 3
gatcctgagc accgaccaca cgggtcc                                              27

<210> SEQ ID NO 4
<211> LENGTH: 27
<212> TYPE: DNA
<213> ORGANISM: Artificial Sequence
<220> FEATURE:
<223> OTHER INFORMATION: SLC29A2-N57D Reverse

<400> SEQUENCE: 4
ggacccgtgt ggtcggtgct caggatc                                              27
```